(12) United States Patent
Yen

(10) Patent No.: US 9,504,641 B2
(45) Date of Patent: *Nov. 29, 2016

(54) THERAPY TO REDUCE EXTRAVASATION DAMAGE

(76) Inventor: Richard C. K. Yen, Yorba Linda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/605,765

(22) Filed: Sep. 6, 2012

(65) Prior Publication Data

US 2013/0064865 A1    Mar. 14, 2013

Related U.S. Application Data

(60) Provisional application No. 61/573,630, filed on Sep. 10, 2011, provisional application No. 61/627,623, filed on Oct. 14, 2011.

(51) Int. Cl.

| | |
|---|---|
| *A61K 38/16* | (2006.01) |
| *A61K 31/4709* | (2006.01) |
| *A61K 35/18* | (2015.01) |
| *A61K 35/14* | (2015.01) |
| *A61P 7/04* | (2006.01) |
| *A61K 38/36* | (2006.01) |
| *A61P 7/00* | (2006.01) |
| *A61P 31/00* | (2006.01) |
| *A61P 33/06* | (2006.01) |
| *A61P 39/06* | (2006.01) |
| *A61K 9/14* | (2006.01) |
| *A61K 35/16* | (2015.01) |
| *A61K 9/00* | (2006.01) |
| *A61K 9/50* | (2006.01) |
| *A61K 9/51* | (2006.01) |
| *A61K 9/10* | (2006.01) |

(52) U.S. Cl.
CPC .......... *A61K 9/0019* (2013.01); *A61K 9/5052* (2013.01); *A61K 9/5169* (2013.01); *A61K 38/363* (2013.01); *A61K 9/10* (2013.01)

(58) Field of Classification Search
None
See application file for complete search history.

(56) References Cited

U.S. PATENT DOCUMENTS

| | | | |
|---|---|---|---|
| 6,221,668 B1 * | 4/2001 | Ryan et al. | ............ 436/8 |
| 6,262,019 B1 | 7/2001 | Keller et al. | |
| 6,916,795 B1 | 7/2005 | Youssef | |
| 2002/0142046 A1 * | 10/2002 | Yen | ............ 424/491 |
| 2009/0304804 A1 * | 12/2009 | Yen | ............ 424/499 |
| 2010/0279939 A1 * | 11/2010 | Fries et al. | ............ 514/15.3 |
| 2011/0189299 A1 * | 8/2011 | Okubo et al. | ............ 424/491 |

OTHER PUBLICATIONS

Smiley et al. "Fibrinogen stimulates macrophate chemokine secretion through toll-like receptor 4" J Immunol. Sep. 1, 2001; 167(5) abstract.*
Perdomo et al. "Quinine-induced thrombocytopenia: drug-dependent GPIb/IX antibodies inhibit megakaryocyte and proplatelet production in vitro". Blood Jun. 2, 2011 vol. 117 No. 22 5975-5986.*
Reiter et al. "Vitamin E and excessive bleeding" Ugeskr Laeger, Dec. 5, 2005; 167(49) (abstract).*
Manjunatha Antiboagulant proteins from snake venoms:structure, function and mechanism. Biochem J. (2006) 397, 377-387.*
Dr. Anrei Gudkov, Radiation Sickness Cures and Anti-Radiation Pills, http://nextbigfuture.com/2009/07/radiation-sickness-cures-and-anti.html, Jul. 20, 2009.

* cited by examiner

*Primary Examiner* — Robert A Wax
*Assistant Examiner* — Danah Al-Awadi
(74) *Attorney, Agent, or Firm* — David Guerra

(57) ABSTRACT

A method of treating a patient who has extravasation of blood from an intravascular compartment to an extravascular compartment. An agent is administered to the patient which mitigates a harmful effect of break-down products of blood at an extravascular site, resulting in the patient having reduced morbidity and mortality. The morbidity and mortality of the patient is further reduced by concomitant administration of a suspension of submicron protein spheres having a molecular weight of ranging from 780 billion Daltons to less than 0.8 billion Daltons.

15 Claims, No Drawings

THERAPY TO REDUCE EXTRAVASATION DAMAGE

CROSS-REFERENCE TO RELATED APPLICATION

This application is an U.S. non-provisional utility application under 35 U.S.C. §111(a) based upon U.S. provisional applications 61/573,630 filed on Sep. 10, 2011 and 61/627,623 filed on Oct. 14, 2011. Additionally, this U.S. non-provisional utility application claims the benefit of priority of U.S. provisional applications 61/573,630 filed on Sep. 10, 2011 and 61/627,623 filed on Oct. 14, 2011. The entire disclosures of the prior applications are incorporated herein by reference.

BACKGROUND OF THE INVENTION

Field of the Invention

The present invention relates to the field of therapy for patients who have extravasation of blood internally, due to exposure to lethal or sub-lethal doses of radiation and other causes, with special attention to the reduction of the damage caused by the presence of break-down products from blood cells in the extravascular site.

The disclosed therapy comprises oral, intramuscular, subcutaneous, intraperitoneal and intravenous administration of agents that can bind or mitigate the effects of the break-down products of blood cells that have leaked into the extravascular space.

Description of the Prior Art

Exposure to massive doses of ionizing radiation, such as after a dirty-bomb or atomic-bomb explosion, or a nuclear-reactor or medical radiation accident, —whether the dose is definitely lethal (or sublethal if the patient has no co-morbidity)—can lead to major morbidity and/or mortality. If the victim survives the direct effect of the bomb blast, he still may suffer from damages to the nervous, digestive, pulmonary, hematopoietic and other vital systems. Published articles have revealed that transfusion of blood components, e.g. red blood cells and platelets can decrease the morbidity and mortality among irradiated patients. There is however, little attention paid to the effect of blood cells, e.g. red cells and white cells, which have leaked into the extravascular space which can cause the body to react in ways detrimental to the healing process needed to recover from the effects of irradiation.

One group of patients is particularly susceptible to the ill effects of suboptimal concentrations of red blood cells, white blood cells and platelets in vivo after exposure to irradiation, burn and chemotherapy. These are patients who are on anti-platelet treatment or anti-coagulation treatment for a variety of reasons. They become anemic and thrombocytopenic because they have excessive internal bleeding leading to increased morbidity and mortality compared to patients who are not on such anti-platelet or anti-coagulation treatments. These are the same patients who will have an excessive load of blood cells in the extravascular compartments, which will break down and cause inflammatory responses which will overwhelm the body's healing responses.

Various methods have been employed to treat radiation sickness, all of them not focused on dealing with the presence of break-down products in the extravascular compartment. For example: (1) Neumune, an androstenediol, had been used by the US Armed Forces Radiobiology Research Institute under joint development with Hollis-Eden Pharmaceuticals; (2) A Chinese herbal medicine called Cordyceps sinensis had been used to try to protect the bone marrow and digestion systems of mice after whole body irradiation; (3) Bisphosphonate compounds had also been tried; (4) U.S. Pat. No. 6,916,795 disclosed an "energy-protective composition" comprising adenosine phosphates; (5) Garnett and Remo disclosed at the International Symposium on Application of Enzymes in Chemical and Biological Defense, Plenary Session Abstract, May 2001 that "DNA Reductase" had some "Opportunist Clinical Activity Against Radiation Sickness"; and (6) U.S. Pat. No. 6,262,019 disclosed a composition called MAXGXL which contains glytathione. All of the above are soluble enzymes, steroids or small molecules.

Of particular interest is the discussion listed under: http://nextbigfuture.com/2009/07/radiation-sickness-cures-and-anti.html It discussed:

(1) the effect of a small-molecule inhibitor to the p53-mediated apoptosis. A single shot of this drug, called CBLB502, at less than 1% of the maximum dose resulted in an 87% survival rate of mice exposed to an otherwise lethal dose of 13 Gray of radiation. By comparison, even at the maximum dose of the second-best chemical, called amifostine, only 54% of similarly irradiated mice survived.

(2) The work done at the Boston University School of Medicine on new compounds called the "EUK-400 series" which may be taken orally.

(3) DARPA funded work done at the Rice University called "Nanovector Trojan Horses, NTH." These carbon nanotube-based drugs may scavenge free radicals and mitigate the effects of ionizing radiation. As disclosed by the authors, these compounds aim at the mitigation of the free radicals generated directly by the ionizing radiation and not at the breakdown products of blood cells, or caused by the blood cells, in the muscles, the tissues surrounding the nerves, the intestine, and other vital organs.

All of the above treatments employ mechanisms very different from the present invention. While some of the above mentioned treatments may result in improved survival of irradiated patients, it is not clear if the survivors will have other long-term medical problems caused by the irradiation or by the treatment. Therefore there is need for a new treatment that will improve survival, yet with less or no long-term medical problems among the survivors, caused either by the radiation or by the side-effects of the treatment.

Yen has disclosed a novel product useful to replace natural platelets, which can decrease the escape of blood cells from the intravascular system. The disclosures include: (a) the U.S. provisional patent application filed on Sep. 10, 2011, application No. 61/573,630, entitled "Submicron particles to decrease need for transfusion"; (b) the U.S. provisional patent application filed on Oct. 14, 2011, application No. 61/627,623, entitled "Submicron particles to decrease need for transfusion in some patients"; (c) the U.S. non-provisional patent application filed on Sep. 6, 2012, application Ser. No. 13/604,770 entitled "Submicron particles to decrease transfusion." The entire disclosures of these prior applications are incorporated herein by reference. However, the disclosed invention deals with decreasing the leakiness of blood vessels and not with a therapy to deal with the removal of blood cells already leaked into the extravascular compartments or the mitigation of the effect of leaked blood cells, including red cells, white cells, platelets and plasma.

The break-down products include and not limited to: (a) cell membrane, which typically contains lipids that would provoke inflammatory responses; (b) enzymes; (c) nucleic acids (e.g. DNA and RNA from the white cells); but more importantly (d) hemoglobin and its further break-down products of (e) heme, (f) other iron species, (g) other globin molecules. Hemoglobin molecules outside the confinement of a red cell membrane is highly toxic to the body. It is well known that hemoglobin molecules can bind nitric oxide and other molecules which are vital in the maintenance of vasodilation. That is why when hemoglobin solutions (instead of red cells) are transfused in an attempt to resuscitate patients who have suffered massive blood loss, the result is always vasoconstriction and hypertension, leading to even less oxygen being delivered to the hypoxic tissues, which can actually accelerate death. Few studies in the literature have suggested that cellular break-down products can have a major impact on the survival of patients after a massive dose of irradiation. Therefore the approach of using drugs and other agents to facilitate the removal of the break-down products, or to mitigate their effects in the extravascular compartment is a novel and non-obvious invention.

In this application the term "improved survival" or "to improve survival" can mean (1) a prolong survival time, e.g. if 100% of the irradiated subjects will die before day-30 without treatment, a treatment will be considered effective in prolonging life if it takes longer than 30 days (e.g. a year) before 100% of a similarly irradiated group dies (possibly from other problems); (2) an increase in the survival rate at a fixed time (e.g. 30-day survival rate, or 90-day survival rate) after irradiation. Also the irradiation dose can be maximally lethal, leading to 100% of the irradiated subjects dying if untreated; or minimally lethal, having only, e.g. 5% of the irradiated subjects dying—both will be called "a lethal dose of irradiation."

It is expected that augmentation of the effects of the present invention is possible, by the concomitant use of additional therapies, e.g. (a) by decreasing blood loss from the intravascular compartment, (b) by increasing oxygen delivery through transfusion of red cells and platelets, (c) by the use of bone marrow stimulating molecules so that the body can generate new red cells and new platelets faster, (d) by additional supportive therapy.

However, it would be most preferable that the new method of treatment disclosed here will be able to improve survival all by itself without the use of any blood transfusion or the use of any prior-art treatment for irradiated patients.

Indeed the administration of the present invention is expected to decrease the need for other therapy which had been used or attempted to be used to improve the morbidity and mortality of patients, before and after exposure to irradiation, e.g. the transfusion of blood components to these patients.

The term "blood component" in this invention can mean any protein and non-protein component extracted from blood, or a product manufactured in vitro as a molecule or as a recombinant product based on the gene or genes known to code for the naturally-made blood component. It can include cellular and non-cellular components of blood.

Examples in this application include patients exposed to radiation. It is to be understood that the beneficial effects of the present invention is not limited to irradiated patients, but will include all patients who suffer from leaky endothelium, resulting in blood cells escaping into the extravascular compartment. Examples will also include people exposed to thermal burns (external and internal), radiation burns, viral infections that cause bleeding, or people suffering from thrombocytopenia due to cancer, chemotherapy, and all kinds of procedures requiring transfusion of different kinds of blood cells to increase cell counts, such as patients who are septic or undergoing disseminated intravascular coagulation (DIC), thrombotic or hemorrhagic episodes, idiopathic (or immunological) thrombocytopenic purpura (ITP) or surgical patients.

Abkowitz et al disclosed a list of heme-binding agents in U.S. Pat. No. 8,119,773 B2. However, the authors used the heme-binding agents to facilitate heme-iron export from intact cells. There was no teaching on using heme-binding agents for the resuscitation of patients who have cell breakdown products in the extravascular compartment.

The various compositions of the red cell membrane which need to be removed when present in the extravascular compartment can be found in: http://medtextfree.wordpress.com/2011/December/26/chapter-27-the-red-cell-membrane/.

We expect macrophages are involved in the clean-up of extravascular hemoglobin and extravascular membrane material. Both classically-activated macrophages (with Th1-like phenotype) and the alternatively-activated macrophages (with Th2-like phenotype) may be involved. The process may be different from what happens in the healthy body. In the healthy body, old erythrocytes are routinely phagocytized by macrophages in the spleen, liver and bone marrow, but the process does not leak free hemoglobin to the extracellular medium because the whole erythrocyte is degraded within the macrophage.

Part of the information disclosed in this application was filed with the USPTO as a commonly owned U.S. provisional application, No. 61/281,466 ("Submicron Particles for the Treatment of Radiation Damage in Patients") and as a commonly owned U.S. non-provisional application, Ser. No. 12/927,543 filed on Nov. 16, 2010 with the same title. The entire disclosures of these prior applications are incorporated herein by reference.

Examples of Anti-Platelet and Anti-Coagulation Medication and Molecules

There are many anti-platelet products on the market. The following list provides only a sample of some of the known medications in the field:

1. ADP-receptor inhibitors: e.g. Cangrelor, Clopidogrel, Elinogrel, Prasugrel, Ticagrelor, Ticlopidine;
2. Aspirin;
3. GpIIb/IIIa inhibitors: e.g. abciximab, Eptifibatide, Tirofiban, and antibodies such as anti-CD41; and
4. Other candidates: e.g. Aloxiprin, Carbasalate, Cilostazol, Cloricromen, Clorindione, Dipyridamole, Ditazole, Indobufen, Picotamide, Ramatroban, Terbogrel, Terutroban, Trifusal.

Common anti-coagulation medications that thin blood by having mechanisms against coagulation factors include: heparin, warfarin, enoxaparin. Others inhibitors include direct thrombin-inhibitors (e.g. argatroban, lepirudin, bivalirudin, dabigatran, ximelagatran.) Still others inhibit factor Xa, e.g. Fondaparinux, Idraparinux, Rivaroxabin, Apixaban.

Examples of Agents that can Bind Heme and Other Break-Down Material from Blood Cells List of agents that bind to or mitigate the harmful effects of heme (a metalloporphyrin) include the following:

I. Proteins mentioned in ""The Influence of heme-binding proteins in heme-catalyzed ozidations"" by Vincent S H et al., Arch Biochem Biophys. 1988, September; 265(2):539-50" include: Hemopexin, Human albumin, Glutathione S-transferases, Liver Fatty acid-binding proteins II. Examples of antimalaria agents mentioned in ""Characterization of noncovalent complexes of antimalarial agents etc"" by Pashynska V A et al., J Am Soc Mass Spectrom. 2004, August; 15(8):1181-90": Quinine, Artemisinin, Dihydroartemisinin, Alpha- and Beta-artemether, Beta-arteether III. List of Heme-bind agents mentioned in ""Compositions and Methods for Facilitating Heme-Iron Export from Cells"" by Abkowitz et al., U.S. Pat. No. 8,119,773 B2, Feb. 21, 2012" include: Hemopexin, Synthetic heme binders, Bacterial Hemophores, Heme-binding protein 23 (HBP23; Peroxiredoxin 1, or Prx 1), Adrenal Inner Zone Antigen (IZA1), Rhodnius Heme-binding Protein (RHBP), NADPH-dependent Methemoglobin Reductase, Histidine-rich Protein 2 (HRP-2), Damage Resistance Protein 1 (Dap1p), HupA, Periplasmic Lipoprotein (HpbA), ShuT, PhuS, HemS, Bacterial Heme-binding Protei, Heme-binding agent with a heme-binding site having two histidines that are 43-52 amino acids apart and hydrophobic amino acids lining a heme binding pocket IV. Chelators (Common or Synthetic)

Common chelators include citrate; desferrioxamine; 2,2'-bipyridine; nitrolotriacetic acid; 2,3-dimercapto-1-propanol (BAL); edathamil calcium disodium (CaEDTA); EDTA; d-penicillamine; 1,10-phenanthroline; bathophenanthroline sulfonate; N,N'-ethylenebis(o-hydroxyphenylglycine); 2,3-dihydroxybenzoic acid; catechol; tropolone; N,N'-bis(2,3-dihydroxybenzoyl)-1,6-diaminohexane.

Synthetic chelating agents include derivatives of pyridoxal or 2-hydroxybenzaldehyde and isonicotinic acid hydrazide or benzhydrazide, e.g. pyridoxal isonicotinoyl hydrazone, pyridoxal benzoyl hydrazone, 2-hydroxybenzal isonicotinoyl hydrazone, 2-hydroxybenzal benzoyl hydrazone, pyridoxal-valine Schiff base, pyridoxal.

V. Antioxidants (Reducing agents) include: Ascorbic acid, Thiols, Polyphenols, Glutathione, Lipoic Acid, Uric Acid, Carotenes, Alpha-Tocopherol, Ubiquinol.

SUMMARY OF THE INVENTION

In view of the foregoing disadvantages inherent in the known types of treatment methods now present in the prior art, the present invention provides a new and improved therapy for patients who have extravasation of blood internally and overcomes the above-mentioned disadvantages and drawbacks of the prior art. As such, the general purpose of the present invention, which will be described subsequently in greater detail, is to provide new and improved therapy for patients who have extravasation of blood internally, due to exposure to lethal or sub-lethal doses of radiation and other causes, which has all the advantages of the prior art mentioned heretofore and many novel features that result with special attention to the reduction of the damage caused by the presence of break-down products from blood cells in the extravascular site which is not anticipated, rendered obvious, suggested, or even implied by the prior art, either alone or in any combination thereof.

To attain this, the present invention essentially comprises a new treatment of patients who have extravasation of blood internally due to exposure to damaging doses of radiation and other causes. The new treatment aims at the removal of break-down products of blood cells in the extravascular compartment or mitigation of their harmful effects. The new treatment can be administered orally, intramuscularly, subcutaneously, intraperitoneally or intravenously. Administration of said compounds or agents before and after exposure to danger reduces the morbidity and mortality of the patients with or without concomitant application of conventional measures such as the transfusion of blood components or a suspension of protein spheres to improve the condition of the patient.

Even still another object of the present invention is to provide a method of treating a patient who has extravasation of blood from the intravascular compartment to the extravascular compartment, comprising administration of an agent which mitigates the harmful effect of the break-down products of blood at the extravascular site, resulting in said patient having reduced morbidity and mortality.

There has thus been outlined, rather broadly, the more important features of the invention in order that the detailed description thereof that follows may be better understood and in order that the present contribution to the art may be better appreciated.

The invention may also include a method to treat patients who have extravasation of blood internally.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide new and improved submicron particles to decrease transfusion that has all of the advantages of the prior art treatment methods and none of the disadvantages.

It is another object of the present invention to provide new and improved therapy for patients who have extravasation of blood internally that may be easily and efficiently manufactured and marketed.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

DETAIL DESCRIPTION OF THE INVENTION

It has been found according to the present invention that:
1. a suspension of submicron protein particles which do not contain any biological molecule known to be involved with blood coagulation can be used effectively to treat patients who have been harmfully irradiated, said irradiation results in leakage of blood into the extravascular compartment, said treatment results in reduced morbidity, such as anemia and fatigue and reduced mortality.

2. a suspension of submicron protein particles which contain biological molecules known to be involved with blood coagulation, such as coagulation factors, can be used effectively to treat patients who have been harmfully irradiated, said irradiation results in leakage of blood into the extravascular compartment, said treatment results in reduced morbidity, such as anemia and fatigue, and mortality.

3. an agent known to bind heme can be administered intraperitoneally to a patient who has been irradiated, said irradiation results in leakage of blood into the extravascular compartment, said treatment with heme-binding agent results in reduced morbidity and mortality of the patient.

4. a number of agents, such as those listed in this invention, known to bind to or mitigate the harmful effect of heme can be administered to a patient who has been irradiated, said irradiation results in leakage of blood into the extravascular compartment, said treatment with said agents results in reduced morbidity and mortality of the patient.

5. a number of agents, such as those listed in this invention, known to bind to or mitigate the harmful effect of heme can be administered to a patient who has been irradiated, said method of administration can be oral, subcutaneous, intramuscular, intraperitoneal, or intravascular, depending on the stability and safety of the agent, said irradiation results in leakage of blood into the extravascular compartment, said treatment with said agents results in reduced morbidity and mortality of the patient.

6. a number of agents, such as those listed in this invention, known to bind to or mitigate the harmful effect of heme can be administered to a patient who has been irradiated, said administration of said agent comprised administration of a dose high enough to achieve its medical effect but below the maximally tolerated dose by the safest route, said irradiation results in leakage of blood into the extravascular compartment, said treatment with said agents results in reduced morbidity and mortality of the patient.

7. a number of agents, such as those listed in this invention, known to bind to or mitigate the harmful effect of heme can be administered concomitantly with a suspension of submicron protein particles which do not contain any biological molecule known to be involved with blood coagulation, said suspension of protein particles is to be administered intravenously, to a patient who has been irradiated, said irradiation results in leakage of blood into the extravascular compartment, said concomitant treatment with said agents and the administration of a suspension of submicron protein particles results in greatly reduced morbidity and mortality of the patient.

8. a number of agents, such as those listed in this invention, known to bind to or mitigate the harmful effect of heme can be administered concomitantly with a suspension of submicron protein particles which contain biological molecules known to be involved with blood coagulation, such as coagulation factors, said suspension of protein particles is to be administered intravenously, to a patient who has been irradiated, said irradiation results in leakage of blood into the extravascular compartment, said concomitant treatment with said agents and the administration of a suspension of submicron protein particles results in greatly reduced morbidity and mortality of the patient.

9. the treatment will result in the patient needing less blood components during the sick period compared to similarly affected patients who are not administered the present invention. The reduced need is reflected in fewer episodes of transfusion or a smaller quantity of transfused material during the sick period.

10. the treatment will result in the patient needing no blood component transfusion during the sick period.

It has also been found according to the present invention that:

11. in anticipation of the need of the above-mentioned patients in item 1 to item 10, the present invention can be administered as a prophylactic measure before the patient becomes symptomatic and the present invention will result in less need of blood component transfusions and in greatly reduced morbidity and mortality of the patient.

12. treatment with the present invention in certain groups of patients, including the above-mentioned patients in items 1 to 11, and particularly patients who are under anti-platelet therapy for a variety of reasons will greatly reduced the morbidity and mortality of these patients.

13. patients taking anti-coagulation medication that can thin blood by a variety of mechanisms can also have decreased morbidity and/or mortality by treatment with the present invention.

14. the sizes of the spheres in the sphere suspension can range from 1.0 micron to less than 0.1 micron in diameter. These sizes correspond to a weight (gram per sphere) in the range from 128E-14 (i.e. one hundred twenty eight to the exponent of negative 14, base 10) to 0.13E-14 (i.e. about zero point one-three to the exponent of negative 14, base 10), respectively; with the median weight of the spheres being 2.8E-14 gram per sphere. In terms of molecular weight, the range of the spheres within the population ranges from 780E+9 Daltons on the high side to about 0.78E+9 Daltons on the low side, respectively, with the median molecular weight of the spheres being 17E+9 Daltons.

Although specific embodiments of the present invention will now be described, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the claims or appended claims.

Experiment One

Manufacture of Submicron Particles Small Enough to Remain in Suspension for Over a Year in Room Temperature Purpose:

To disclose a method of mass-production of a suspension of particles that are essentially spherical and with a median diameter of less than one micron, manufactured from a high concentration of animal albumin.

Material and Method:

Bovine serum albumin powder was purchased from Boval Company LP, Cleburne, Tex. and dissolved in water to result in an 18% solution. The solution will be further processed as follows without the addition of surfactants or detergents. Glutaraldehyde solution was purchased from Sigma-Aldrich, St. Louis, Mo. 63103 and diluted to 0.15 mg per ml with water. A mixture of alcohol to be called EG was prepared as follows: 2850 ml of 100% ethanol USP grade was mixed with 950 ml of water, after which 7.6 ml of a glutaraldehyde solution (25%) and 114 ml of a sodium chloride solution (0.9%, USP) was added to result in 3921.6 ml of EG solution. Sorbitol powder USP grade was purchased from Sigma-Aldrich and dissolved in water to form a 25% solution. Sodium caprylate was purchased from Jost Chemical Co., St. Louis, Mo. 63114 and dissolved in water to form a 10% solution.

The following steps were done at room temperature, 19° C. to 24° C. under sterile conditions. All the solutions were filtered via 0.2 micron filters before mixing in a class-100 clean room. At time zero, 190 ml of glutaraldehyde solution (0.15 mg/ml) was added to 381 ml of bovine serum albumin solution (18%) and well mixed in the container. Within 3 minutes, 3426 ml of EG was added and well mixed, at which time the solution turned turbid indicating the formation of spheres.

After one hour, the suspension was dialyzed in distilled water to remove the EG. After measuring the concentration of the spheres in the dialyzed suspension, sorbitol, caprylate and an additional aliquot of distilled water were added to the dialyzed suspension to result in a final concentration, respectively, of 5% sorbitol, 13.3 mg of caprylate per gram of total protein, and 8 mg of spheres/ml of suspension.

The suspension was subsequently filled into sterile containers, capped and sealed. Then the product was terminally sterilized by heating the suspension inside the container to 60 degrees Centigrade for 10 hours, or pressurized up to 600 MPa.

Results:

Analysis of the suspension showed that the particles are spherical and the median diameter was about 0.35 micron, with less than 1% of the sphere with diameter greater than one micron. No aggregates were observed. The suspension was stable after one year of storage in room temperature without constant agitation to keep the particles in suspension. There was no significant shift of size distribution of particles after one year of storage in room temperature.

The suspension was frozen and kept frozen at minus 18° C. for at least one year. Then samples were thawed and stored at room temperature for at least one year. Analysis of the size distribution of particles showed no significant change from the size distribution of particles in suspensions analyzed within days of completion of synthesis and terminal sterilization.

The density of the spheres is between 1.0 and 1.1 relative density since they do not settle to the bottom during prolong storage but are kept in suspension by the Brownian movement of the supernatant. Measurement of the size and molecular weight of the spheres showed that spheres with diameter of 1 micron and 0.1 micron have molecular weight of $780 \times 10^9$ Daltons and $0.78 \times 10^9$ Daltons, respectively. The same can be written as 780E+9 and 0.78E+9, respectively. The one micron spheres have a weight of about $128 \times 10^{-14}$ gram per sphere. The 0.1 micron spheres have a weight of about $0.13 \times 10^{-14}$ gram per sphere.

Comments:

Although bovine albumin solutions are used in this experiment, it is anticipated a number of other albumin solutions can be used, including human serum albumin (dialyzed in distilled water, or not dialyzed), other natural (human or animal) albumin or albumin molecules produced by recombinant-DNA methods. In addition, other proteins may be used to produce spheres with comparable functionality, including fibrinogen, immunoglobulin, collagen, gelatin, as disclosed in U.S. Pat. No. 5,069,936 by Yen.

Although the spheres are not further coated with any other biologically active molecules during the manufacturing process in this experiment, it is anticipated that a number of other biologically active molecules, including coagulation factors, such as fibrinogen, vonWillebrand factor, Factor IX and other coagulation factors may be added to the spheres during the manufacturing process. It is expected that various ratios of mixing of the biologically active molecule solution with the sphere suspension are permissible. Specifically, experiments have been conducted where, for example, a solution of fibrinogen up to 3 mg/ml may be mixed at a ratio of 1 part (by volume) of the fibrinogen solution to 4 parts (by volume) of the sphere suspension (the turbid suspension after addition of EG, and before dialysis of the EG-containing suspension with distilled water) to result in "coated spheres." See PCT/US2008/006014 by Yen.

Although a specific concentration of ingredient solutions are mentioned here as an example, other higher or lower concentrations can be used when combined with a compatible compensating concentration of other ingredients. For example, albumin solutions can vary between 5% to 20% in initial concentration before the addition of a glutaraldehyde solution, which can vary from 0.05 to 0.5 mg/ml. The concentration of ethanol in the EG mix can vary from 55% to 100%, while the glutaraldehyde concentration in EG can vary from 0.1 mg to 0.75 mg/ml and the sodium chloride concentration can vary from 0.5 to 0.005 mg/ml in the EG mix.

It is surprising that a suspension of protein sphere can undergo heating at 60 degree Centigrade for 10 hours without forming aggregates or clumps. The addition of sorbitol together with caprylate probably has a synergistic effect on protecting the protein spheres from aggregation or expression of new antigenic sites during the process of heating and subsequent cooling to room temperature.

Experiment Two

The Harmful Effect of Blood Leakage from the Intravascular Compartment to the Extravascular Compartment as a Result of Irradiation Purpose:

To find out if the extravasation of blood from the intravascular compartment to the extravascular compartment can be a major cause of morbidity and mortality and whether the administration of fibrinogen-coated albumin spheres (FAS) can decrease such leakiness of blood vessels Materials and Methods:

FAS were manufactured with human serum albumin, coated with human fibrinogen molecules, and subjected to a terminal sterilization step essentially as described in Experiment One. The median diameter of the spheres in the suspension was about 0.4 micron. Less than 1% of the spheres had diameters larger than one micron. Mice were irradiated on day-zero with gamma radiation known to cause a mortality rate of 70% (LD70.) Test and control articles were administered intravenously to animals via the tail vein, at 24 hours, day-5 and day-10 after irradiation. Survival rate was scored on day-30.

Results:

There were 3 groups of mice (10 animals per group): (1) irradiated mice treated with normal saline (1 ml/kg, i.v.); (2) irradiated mice treated with submicron particles (8 mg/kg, equal to 1 ml/kg, i.v.); (3) mice not irradiated but treated with submicron particles (8 mg/kg). The results showed that all the animals in group (3) survived to the end of the experiment with no clinical signs or ill effect, when they were sacrificed. The survival rate of mice in group (1) and group (2) was 30% and 70%, respectively. The improvement in survival was statistically highly significant (P<0.01).

The experiment was repeated with mice administered with an anti-platelet medication. A mild dose of irradiation (which causes no mortality in mice not given any anti-platelet medication or agent) resulted in a mortality rate of 90% in mice administered with an anti-platelet agent. At least 10% of the mice died from bleeding from the intestine and about 50% from intracranial hemorrhage Serial measurements of the intravascular "hemoglobin concentration" (i.e. hemoglobin concentrations within erythrocytes) and red cell counts showed that mice administered with an anti-platelet agent but without the administration of FAS lose red cells from the intravascular compartment into the extravascular compartment far faster than mice treated with an anti-platelet agent but also receive FAS. Survival rate in the control group was 10% while the group treated with the FAS was 70%.

Comments:

The data clearly showed that extravasation of blood from the intravascular compartment into the extravascular compartment is a major cause of mortality. The two groups of mice treated with irradiation and an anti-platelet agent both become anemic because of the shut-down of red cell production from the bone-marrow. However, the group not receiving FAS had greater extravasation than the group receiving FAS. The improvement from a 10% survival rate due to more leaky blood vessels to the 70% survival rate due to protected blood vessels proved that mortality is not just due to anemia or lack of red cells inside the intravascular system, but to a greater degree due to the presence of red cells and other blood cells and their break-down products in the extravascular compartment. The data suggest strongly that mitigation of the harmful effects of the break-down product of blood cells at the extravascular site can reduce morbidity and mortality of the patient.

Submicron particles administered intravenously at 8 mg/kg to animals exposed to lethal doses of ionizing radiation improved their survival rate. More experiments need to be done to see if a lower or higher dose of the particles will provide similar or better results.

Although this experiment used submicron particles already coated with fibrinogen, it is anticipated that blank submicron particles not coated with any biologically active molecule during the synthesis steps may be equally effective, or even better.

Although Experiment Two and Three described animals exposed to irradiation, the data reveal that submicron protein spheres of the present invention can be medically useful in medical, surgical, and trauma patients who need blood component treatment. The present invention does not involve molecules that stimulate blood cell production. The present invention is not a growth factor; it does not require the body to have sufficient number of progenitor cells which are to be stimulated. The present invention works immediately and is unlike stimulant molecules that need several days before the body can produce enough of its own blood cells (red blood cells, white blood cells or platelets) to affect clinical bleeding.

Ethical treatment of animals does not allow the use of animals larger than mice or rats to be used in large numbers for the study of the effect of transfusion in animals exposed to a variety of radiation doses, including LD90. Published data have shown that in large animals, transfusion of blood products and other medicine (listed in the Prior Art section) can improve survival. The data here, however, suggest that administration of the present invention will improve survival, with or without the use of other blood components or other medications. The data also suggest that the use of the present invention will decrease the need to use blood components or other medications, in irradiated patients and in patients with other medical and surgical needs.

The fibrinogen content of the spheres used in Experiment Two and Three were found to be about 50 microgram of fibrinogen per mg sphere. New batches of spheres were made using lower concentrations of fibrinogen, resulting in spheres with about 20, 10, 5, and zero microgram of fibrinogen per mg spheres, respectively. All the above preparations of fibrinogen-containing spheres and the no-fibrinogen spheres (blank spheres) were effective in improving the survival of mice after exposure to lethal doses of irradiation. It is expected that in a large-animal model, less blood component transfusion will be needed to improve survival compared to similarly treated animals not administered the present invention of protein spheres with or without fibrinogen attached prior to administration to the patient.

Experiment Three

Administration of Heme-Binding Agents Intraperitoneally to Mitigate the Harmful Effect of Blood Leakage from the Intravascular Compartment to the Extravascular Compartment Purpose:

To find out if the administration of heme-binding agents to reduce the toxic effect of extravasated blood can reduce morbidity and mortality of patients leaking blood from the intravascular compartment.

Materials and Methods:

A group of mice with sufficient number in the group to show a statistical significance between the control group and the treatment group was irradiated with a dose of radiation at LD70. Quinine was purchased from commercial sources and administered at a dose equivalent to 3.7 mg/kg body weight, comparable with a dose of 260 mg given to a 70-kg human. Quinine administered intraperitoneally is known to diffuse to the rest of the body. Quinine was given one hour after exposure to irradiation. FAS were not administered in this experiment.

Result:

The control group of mice had survival rate of about 30%, while the quinine-treated group had survival significantly greater than 30%. The data showed a beneficial effect of an agent binding the heme molecules that had left the intravascular compartment to the extravascular compartment.

Comments:

Although only quinine is used in this experiment, it is expected that the agents listed in this invention can all be medically beneficial to reduce the morbidity and mortality of irradiated patients, whether the agent is a protein, a chelating agent, an antioxidant, an antimalarial agent, or belonging to any other categories.

Although no spheres are administered in this experiment, it is expected that the concomitant administration of a suspension of spheres, whether the spheres contain coagulation factors such as fibrinogen, or not, will further reduce the morbidity and mortality of the patients.

Although the administration of the agent in this experiment is by the intraperitoneal route, any other medically suitable route, be they oral, intramuscular, subcutaneous, intravenous can be used, depending on the nature of the agent (its solubility in water or oil) as well as safety factors.

Although irradiation is used as the cause of extravasation of blood from the intravascular compartment in this experiment, any other cause of morbidity and mortality, such as trauma, burn or allergic reaction to other drugs or allogens can be mitigated with the present invention.

This invention is about a method of treating a patient who has extravasation of blood from the intravascular compartment to the extravascular compartment, comprising administration of an agent which mitigates the harmful effect of the break-down products of blood at the extravascular site, resulting in said patient having reduced morbidity and mortality.

Examples of extravascular compartments will include and not limited to: the muscles, the peritoneum, the surroundings of nerves and nerve bundles, i.e. any compartment surrounding the blood vessels where the components of blood can leak from the intravascular compartment and get trapped within. An extravascular site is anywhere within the extravascular compartment where the blood components have reached and stayed. An extravascular site can also be anywhere outside the extravascular compartment if the containment mechanism of the extravascular compartment is broken, e.g. a muscle group with a torn fiber capsule such that the muscles are exposed; blood elements can reach there even though the site may not be a well contained "compartment."

Morbidity of the patient can be any signs and symptoms consistent with the disease or illness which has been caused by the mechanism producing the extravasation of blood. Morbidity can include and not limited to fever, fatigue, anemia, thrombocytopenia, pancytopenia.

The present invention is a method of treating a patient where the extravasation of blood is caused by any number of causes, including and not limited to trauma, exposure to radiation, to drugs, to infectious agents, and to reactive antigens from external sources. Some of these causes also produce edema due to severe leakiness of the blood vessels.

This invention is a method of treating a patient where the said agent is chosen from a group comprising: proteins, chelating agents, antimalarial agents, heme-biding agents and anti-oxidants. Examples of the above categories of agents have been provided in previous pages. The route of administration will depend on the water- or oil-solubility of the agent and whether the agent can survive in the digestive tract. People skilled with the art of choosing routes for the administration of drugs can easily decide the best route of administration for each above-mentioned agent.

This invention is a method of treating a patient where the administration of an agent comprises: oral, subcutaneous, intramuscular, intraperitoneal, and intravenous route of administration. It should be noted that after a nuclear event, standard forms of health care and their infrastructure may not be available. There may be enough health providers to even start intravenous lines. Therefore, the intraperitoneal route should be considered, where the agent administered into the abdominal cavity can be adsorbed and can reach all the tissues in the body, including sites where blood has extravasated but not easily detectable.

This invention is a method of treating a patient where the break-down products of blood comprise: hemoglobin, heme, globin molecules, cell membrane, lipids from cell membranes, enzymes derived from intracellular sources, DNA and RNA from broken cell nuclei. White cells have nuclei which can break down and release a large amount of DNA and RNA.

This invention is a method of treating a patient who has extravasation of blood from the intravascular compartment to the extravascular compartment, comprising administration of an agent which binds the break-down products of blood at the extravascular site, resulting in said patient having reduced morbidity and mortality. Although binding of the break-down product does not by itself indicate that the harm from the break-down product can be mitigated, the compound that results from the combination of a ligand (such as the agent) and its target (such as lipids or cell membrane fragments) can often facilitate the removal of the toxic material.

This invention is a method of treating a patient where the agent is chosen from a group comprising: proteins, chelating agents, antimalarial agents, heme-binding agents and anti-oxidants.

This invention is again a method of treating a patient where said break-down products of blood comprise hemoglobin, heme, globin molecules, cell membrane, lipids from cell membranes, enzymes derived from intracellular sources, DNA and RNA from broken cell nuclei.

This invention is a method of treating a patient who has extravasation of blood from the intravascular compartment, comprising administration of an agent which stimulates the removal of the break-down products of blood at the extravascular site, resulting in said patient having reduced morbidity and mortality. In other words, the agent may not directly bind the break-down product, but the agent can stimulate cells such as macrophages, or stimulate processes such as cells producing reducing agents to neutralize the effect of oxidative molecules. Agents that stimulate macrophages are well known to practitioners in the art of macrophage sciences.

This invention is a method of treating a patient where stimulation of the removal of the break-down products of blood is by stimulation of the activity of macrophages at the extravascular site.

This invention is a method of treating a patient where the morbidity and mortality of the patient is further reduced by concomitant administration of blood products to the intravascular compartment, comprising: red cells, platelets, plasma and plasma protein fractions. The blood products may be administered intravenously, with a schedule and dosing best suited to be used in combination with the agents described here. There may be synergistic effects since the administration of the agents here may decrease the amount and frequency of blood-component transfusions.

This invention is also a method of treating a patient where the morbidity and mortality of the patient is further reduced by concomitant administration of a suspension of submicron protein spheres where the molecular weight of said protein spheres ranges from 780 billion Daltons to less than 0.8 billion Daltons, said protein spheres having no biologically active molecules added or bound to them prior to patient administration.

This invention is also a method of treating a patient where the morbidity and mortality of the patient is further reduced by concomitant administration of a suspension of submicron protein spheres where the molecular weight of said protein spheres ranges from 780 billion Daltons to less than 0.8 billion Daltons, said protein spheres have at least one coagulation factor bound to them prior to patient administration. The coagulation factor can be any number of the coagulation factors known to medical science, including and not limited to fibrinogen.

This invention is a method of treating a patient where the morbidity and mortality of the patient is further reduced by concomitant administration of a suspension of submicron protein spheres where the molecular weight of said protein spheres ranges from 780 billion Daltons to less than 0.8 billion Daltons, said protein spheres have fibrinogen molecules bound to them prior to patient administration.

This invention is a method of treating a patient where the treatment is prophylactic administration in anticipation of extravasation of blood from the intravascular compartment to the extravascular compartment due to anticipated exposure to radiation, drug reaction, infectious agents and reactive antigen from external sources. In many situations, the patient can anticipate the danger, e.g. workers in a nuclear plant where the plant has experienced a major accident requiring repair immediately, or soldiers going into radioactive areas, or medical providers working in areas where viruses are present that will cause severe extravasation of blood and internal bleeding.

While embodiments of the therapy for patients who have extravasation of blood internally have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of treating a patient who has extravasation of blood from an intravascular compartment to an extravascular compartment, said method comprising the steps of:
   a) preparing albumin spheres comprising the steps of:
   dissolving an albumin powder in water to create an albumin solution; adding a glutaraldehyde solution to said albumin solution;
   adding an alcohol solution to said glutaraldehyde solution and said albumin solution to create a suspension, said alcohol solution comprising ethanol, water, a glutaraldehyde solution, and a sodium chloride solution; dialyzing said suspension in distilled water to remove said alcohol solution from said suspension;
   adding sorbitol, caprylate, and distilled water to said dialyzed suspension to form an albumin sphere suspension;
   wherein said albumin sphere suspension consisting consists of said fibrinogen-coated albumin spheres, said sorbitol, said caprylate, and said additional aliquot of distilled water; and wherein the sizes of the spheres in the sphere suspension range from 1.0 micron to less than 0.1 micron in diameter and there are no aggregates;
   b) administering said albumin sphere suspension to a patient to decrease leakiness of blood from an intravascular compartment into an extravascular compartment resulting in the patient having reduced morbidity and mortality.

2. The method of treating a patient in accordance with claim 1, said extravasation of blood is caused by one selected from the group consisting of exposure to trauma, to radiation, to drugs, to infectious agents, and to reactive antigens from external sources.

3. The method of treating a patient in accordance with claim 1, said albumin spheres are fibrinogen-coated albumin spheres.

4. The method of treating a patient in accordance with claim 1, said step of administering of said albumin spheres is selected from the group consisting of subcutaneous, intramuscular, intraperitoneal, and intravenous route of administration.

5. The method of treating a patient in accordance with claim 1, wherein said albumin spheres have a median diameter of 0.4 micron.

6. The method of treating a patient in accordance with claim 1, where the morbidity and mortality of the patient is further reduced by concomitant administration of blood products to said intravascular compartment, said blood products being selected from the group consisting of red cells, platelets, plasma and plasma protein fractions.

7. The method of treating a patient in accordance with claim 1, wherein said albumin spheres have a molecular weight ranging from 780 billion Daltons to less than 0.8 billion Daltons, said albumin spheres have no biologically active molecules added or bound to said albumin spheres prior to said step of administering of said albumin spheres to the patient.

8. The method of treating a patient in accordance with claim 1 wherein said albumin spheres have a molecular weight of ranging from 780 billion Daltons to less than 0.8 billion Daltons, said albumin spheres have at least one coagulation factor bound to said albumin spheres prior to said step of administering of said albumin spheres to the patient.

9. The method of treating a patient in accordance with claim 1 wherein said albumin spheres have a molecular weight of ranging from 780 billion Daltons to less than 0.8 billion Daltons, said albumin spheres have fibrinogen molecules bound to said albumin spheres prior to said step of administering of said albumin spheres to the patient.

10. The method of treating a patient in accordance with claim 1, wherein said step of administering of said albumin spheres to said patient is performed prior to extravasation of blood from said intravascular compartment to said extravascular compartment and prior to exposure to one selected from the group consisting of radiation, drug reaction, infectious agents and reactive antigen from external sources.

11. A method of treating a patient who has extravasation of blood from an intravascular compartment, said method comprising the steps of:
   a) preparing fibrinogen-coated albumin spheres comprising the steps of:
   dissolving an albumin powder in water to create an albumin solution; adding a glutaraldehyde solution to said albumin solution; adding an alcohol solution to said glutaraldehyde solution and said albumin solution to create a suspension, said alcohol solution comprising ethanol, water, a glutaraldehyde solution, and a sodium chloride solution; adding fibrinogen to said suspension; dialyzing said suspension in distilled water to remove said alcohol solution from said suspension; adding sorbitol, caprylate, and an additional aliquot of distilled water to said dialyzed suspension to form an albumin sphere suspension; wherein said albumin sphere solution consists of said fibrinogen-coated albumin spheres, said sorbitol, said caprylate, and said additional aliquot of distilled water; and wherein the sizes of the spheres in the sphere suspension range from 1.0 micron to less than 0.1 micron in diameter and there are no aggregates;

b) administering said albumin sphere suspension to a patient to decrease leakiness of blood from an intravascular compartment into an extravascular compartment, resulting in the patient having reduced morbidity and mortality; and c) stimulating macrophages at said extravascular compartment to stimulate removal of break-down products of blood at said extravascular compartment.

12. A method of treating a patient who has extravasation of blood from an intravascular compartment to an extravascular compartment, said method comprising the steps of:

a) preparing albumin spheres comprising the steps of:
dissolving an albumin powder in water to create an albumin solution; adding a glutaraldehyde solution to said albumin solution; adding an alcohol solution to said glutaraldehyde solution and said albumin solution to create a suspension, said alcohol solution comprising ethanol, water, a glutaraldehyde solution, and a sodium chloride solution; dialyzing said suspension in distilled water to remove said alcohol solution from said suspension; adding sorbitol, caprylate, and an additional aliquot of distilled water to said dialyzed suspension to form an albumin sphere suspension; wherein said albumin sphere suspension consisting of said albumin spheres, said sorbitol, said caprylate, and said additional aliquot of distilled water; and wherein the sizes of the spheres in the sphere suspension range from 1.0 micron to less than 0.1 micron in diameter and there are no aggregates;

b) administering said albumin sphere suspension to a patient to decrease leakiness of blood from an intravascular compartment into an extravascular compartment, resulting in the patient having reduced morbidity and mortality;

c) wherein said albumin spheres have a molecular weight ranging from 780 billion Daltons to less than 0.8 billion Daltons.

13. The method of treating a patient in accordance with claim 12, wherein said albumin spheres have no biologically active molecules added or bound to said albumin spheres prior to said step of administering of said albumin spheres to the patient.

14. The method of treating a patient in accordance with claim 12, wherein said albumin spheres have at least one coagulation factor bound to said albumin spheres prior to said step of administering of said albumin spheres to the patient.

15. The method of treating a patient in accordance with claim 12, wherein said albumin spheres have fibrinogen molecules bound to said albumin spheres prior to said step of administering of said albumin spheres to the patient.

* * * * *